US005783502A

United States Patent [19]
Swanson

[11] Patent Number: 5,783,502
[45] Date of Patent: Jul. 21, 1998

[54] VIRUS INACTIVATING COATINGS

[75] Inventor: Melvin J. Swanson, Carver, Minn.

[73] Assignee: BSI Corporation, Eden Prairie, Minn.

[21] Appl. No.: 482,872

[22] Filed: Jun. 7, 1995

[51] Int. Cl.$^6$ .................................................. D03D 3/00
[52] U.S. Cl. ................. 442/123; 424/78.17; 424/78.18; 604/360; 428/913
[58] Field of Search ........................ 442/123; 604/360; 424/78.17, 78.18; 428/913

[56] References Cited

U.S. PATENT DOCUMENTS

| | | | |
|---|---|---|---|
| 3,728,213 | 4/1973 | Hinz. | |
| 4,810,567 | 3/1989 | Calcaterra et al. | 428/244 |
| 4,828,912 | 5/1989 | Hossein et al. | |
| 4,847,088 | 7/1989 | Blank | 424/404 |
| 4,865,844 | 9/1989 | Blank et al. | 424/409 |
| 4,929,498 | 5/1990 | Suskind et al. | 428/288 |
| 4,985,023 | 1/1991 | Blank et al. | 604/360 |
| 5,079,004 | 1/1992 | Blank et al. | 424/404 |
| 5,336,305 | 8/1994 | Staats | 106/18.32 |

OTHER PUBLICATIONS

Abstract, Journal of Coated Fabrics; vol. 12; pp. 38–45; "Development of an Organosilicone Antimicrobial Agent for the Treatment of Industrial Surfaces"; Malek et al, Jul. 1982.

Armstrong, J.A. and E.J. Froelich, "Inactivation of Viruses by Benzalkonium Chloride," *Appl. Microbiol.* 12:132 (1964).

Horowitz, "Inactivation of Lipid–Enveloped Viruses in Labile Blood Derivatives by Unsaturated Fatty Acids," *Vox Sang.* 54:14 (1988).

Horowitz, et al., "Inactivation of viruses in labile blood derivatives II. Physical methods," *Transfusion* 25:523 (1984).

Kempf, et al., "Inactivation of Human Immunodeficiency Virus (HIV) by Low pH and Pepsin," *J. Acquired Immune Deficiency Syndrome*, 4:828 (1991).

Morel, et al., "Photochemical Inactivation of Viruses and Bacteriophage in Plasma and Plasma Fractions," *Blood Cells* 18:27 (1992).

Paolantonio, et al., "Low Risk of Transmission of the Human Immunodeficiency Virus by a Solvent–Detergent–Treated Commercial Factor VIII Concentrate," *J. Medical Virology* 36:71 (1992).

Shkurnikova, et.al., "Synthesis of cellulose derivatives containing chemically–bound antiviral substances and study of the effects of their structure on the properties," (*Vysokomolekulyarnye Soedineniya B*, 26(8):605–609 (1984)) (including a non certified English translation thereof).

Sidwell RW and Dixon GJ, "Role of Virucides in Controlling Virus Dissemination by Fabrics," *J. Amer. Oil Chem. Soc.* 46(10):532–6 (1969).

Sidwell RW et.al., "Quantitative Studies on Fabrics as Disseminators of Viruses," *Appl. Microbiol.* 15(4):921–7 (1967).

*Primary Examiner*—Terrel Morris
*Attorney, Agent, or Firm*—Fredrikson & Byron, P.A.

[57] ABSTRACT

Reagents and methods are disclosed for modifying a fabric substrate in order to inactivate viruses, and particularly lipid-enveloped viruses, upon contact. Such substrates can be modified by photochemically immobilizing hydrophilic polymers containing both quaternary ammonium groups and hydrocarbon chains, resulting in a localized surfactancy capable of disrupting lipid-enveloped viruses upon contact with the substrate. Substrates of the invention can be fabricated into the form of articles for medical and related use.

33 Claims, 1 Drawing Sheet

VIRUS INACTIVATING COATINGS

This invention was made in part with government support under 1 R43 AI34225-01 awarded by the National Institutes of Health. The government has certain rights in the invention.

FIELD OF THE INVENTION

This invention relates to medical fabrics, such as those used to prepare surgical gowns, drapes, masks and dressings. In another aspect, the invention relates to porous materials such as those used to prepare filters, membranes, and the like. In yet another aspect, the invention relates to materials and methods for the inactivation of microbial pathogens such as viruses, and in particular, to the inactivation of lipid-enveloped viruses.

BACKGROUND OF THE INVENTION

With the epidemic of AIDS and the risks associated with HIV and other blood borne infectious agents, the protection of health care workers from exposure to potentially pathogenic blood during surgical procedures is a major concern. Fabrics used during surgery and related medical procedures can provide an initial level of protection. Such fabrics can be used to protect patients and health care workers from transmission of pathogens between each other, and to protect either or both against contact with pathogens in their environment.

Common articles used to prevent transmission of pathogens include surgical gowns, drapes, masks, instrument covers and dressings. The use of such articles is typically intended to provide an initial physical barrier to the passage of pathogens. As a result, many protective articles and methods developed to date are intended to either minimize contact between a medical article or biological tissue and a potentially contaminated environment, or else to provide a sterile nontransmissive barrier to the passage of pathogens.

Methods have been described previously for improving the physical barrier provided by medical articles. Applicant's copending U.S. patent application Ser. No. 08/409,534 (filed Mar. 24, 1995 as a continuation of Ser. No. 08/148,157 (filed Nov. 4, 1993)), describes the use of chemical coatings that serve to substantially prevent the passage of pathogenic mediators to or from the surface of articles such as latex gloves.

Aside from the physical protection afforded by fabrics or other materials (with or without coatings), a number of physicochemical methods have previously been used to inactivate pathogens such as viruses. Such methods include exposure to low pH, with or without detergents or proteases (e.g., Hossein, et al., U.S. Pat. No. 4,828,912 and Kempf, et al., *J. Acquired Immune Deficiency Syndrome*, 4:828 (1991)), the use of detergents in combination with solvents or organic acids (e.g., Paolantonio, et al., *J. Medical Virology* 36:71 (1992)), unsaturated fatty acids (e.g., Horowitz, *Vox Sang.* 54:14 (1988)), quaternary ammonium compounds (e.g., Armstrong, J. A. and E. J. Froelich, *Appl. Microbiol.* 12:132 (1964)) and physical methods such as heat (e.g., Horowitz, et al., *Transfusion* 25:523 (1984)) and radiation (e.g., Morel, et al., *Blood Cells* 18:27 (1992)).

Rarely, however, have such physicochemical methods been suggested as useful for preventing the passage of pathogens through protective fabrics or other medically related absorbent materials.

Hinz (U.S. Pat. No. 3,728,213) disclosed an antimicrobial reagent, including antiviral, consisting of alkane pseudoureas immobilized onto cellulose, and included iodine in a form intended to slowly leach out. Shkurnikova, et.al. (*Vysokomolekulyarnye Soedineniya B*, 26(8):605–609 (1984)) showed antiviral activity using several compounds immobilized onto cellulose. However, they were only active when coupled by hydrolytically unstable ester bonds and were not effective when coupled with more stable ether bonds. Sidwell R W and Dixon G J, *J. Amer. Oil Chem. Soc.* 46(10):532–6 (1969) and Sidwell R W et.al., *Appl. Microbiol.* 15(4):921–7 (1967) studied the effects of impregnating fabrics with virucidal agents. These included compounds such as n-alkyl ($C_{14}$, $C_{12}$, $C_{16}$) dimethylbenzyl ammonium chloride, however, the compounds were not covalently immobilized.

It is apparent that in spite of the advances made to date, the industry, and particularly the medical community, are in need of fabrics and other materials that provide improved protection against pathogens, and particularly against lipid-enveloped viral particles.

SUMMARY OF THE INVENTION

The present invention provides an article useful for inactivating viruses upon contact, the article comprising a fabric substrate bearing a coating of immobilized polymers that provide the substrate with nonleachable antiviral activity.

In another aspect, the invention provides novel coating compositions useful for coating a fabric substrate in order to provide it with nonleachable antiviral activity. The composition comprises a plurality of polymer molecules each bearing one or more groups having antiviral activity and one or more photoreactive groups capable of being activated to form covalent bonds with a fabric substrate.

In yet another aspect, the invention provides a method of preparing such an article, the method comprising the steps of:

(a) providing a fabric substrate useful for fabricating a virus contacting article;

(b) providing hydrophilic polymer molecules in bonding proximity to the fabric substrate, the molecules each bearing one or more groups having antiviral activity and one or more photoreactive groups capable of being activated to form covalent bonds with the fabric substrate; and (c) activating the photoreactive groups in order to covalently immobilize the polymer molecules to the surface and provide the resultant coated article with antiviral activity.

The polymer molecules can be applied at any appropriate stage, including to the bulk fabric prior to its formation into an article, or to the formed article itself. In a preferred embodiment, the antiviral groups comprise a plurality of pendant cationic (e.g., quaternary ammonium) groups and a plurality of pendant hydrocarbon chains. The ammonium groups and hydrocarbon chains are together able to interact with a virus in order to render it nonpathogenic.

The present invention provides improved protection against the transmission of viruses in the course of contact between patients and health care workers, as well as protection against contact with viruses in the environment. Since the antiviral agent is covalently immobilized on and/or within the fabric, the article of the present invention avoids the potentially harmful effects associated with an antiviral agent leaching from the fabric onto the skin or into a surgical wound.

Preferably, the fabric is inherently absorbent in order to facilitate the passage of the virus into the material. Once inside the fabric, the virus can be exposed to and inactivated by the immobilized antiviral polymer. The present invention provides a means for rendering otherwise nonwettable fabrics (e.g., nonwoven polyolefins) wettable and absorbent as well as antiviral. In certain embodiments, the fabric is provided with an impermeable barrier backing, e.g., a laminated backing.

The presently preferred coating compositions are unique and useful in a number of respects. In one respect, the compositions are capable of being immobilized onto nonwettable fabrics in a manner that improves the wettability and absorbency of the fabric. In another respect, the compositions are capable of providing nonleachable antiviral activity. These preferred compositions are characterized by their ability to provide a localized surfactant character that inactivates viruses such as lipid-enveloped viruses, presumably by causing disruption of the viral envelopes.

DETAILED DESCRIPTION OF THE INVENTION

Figure 1:
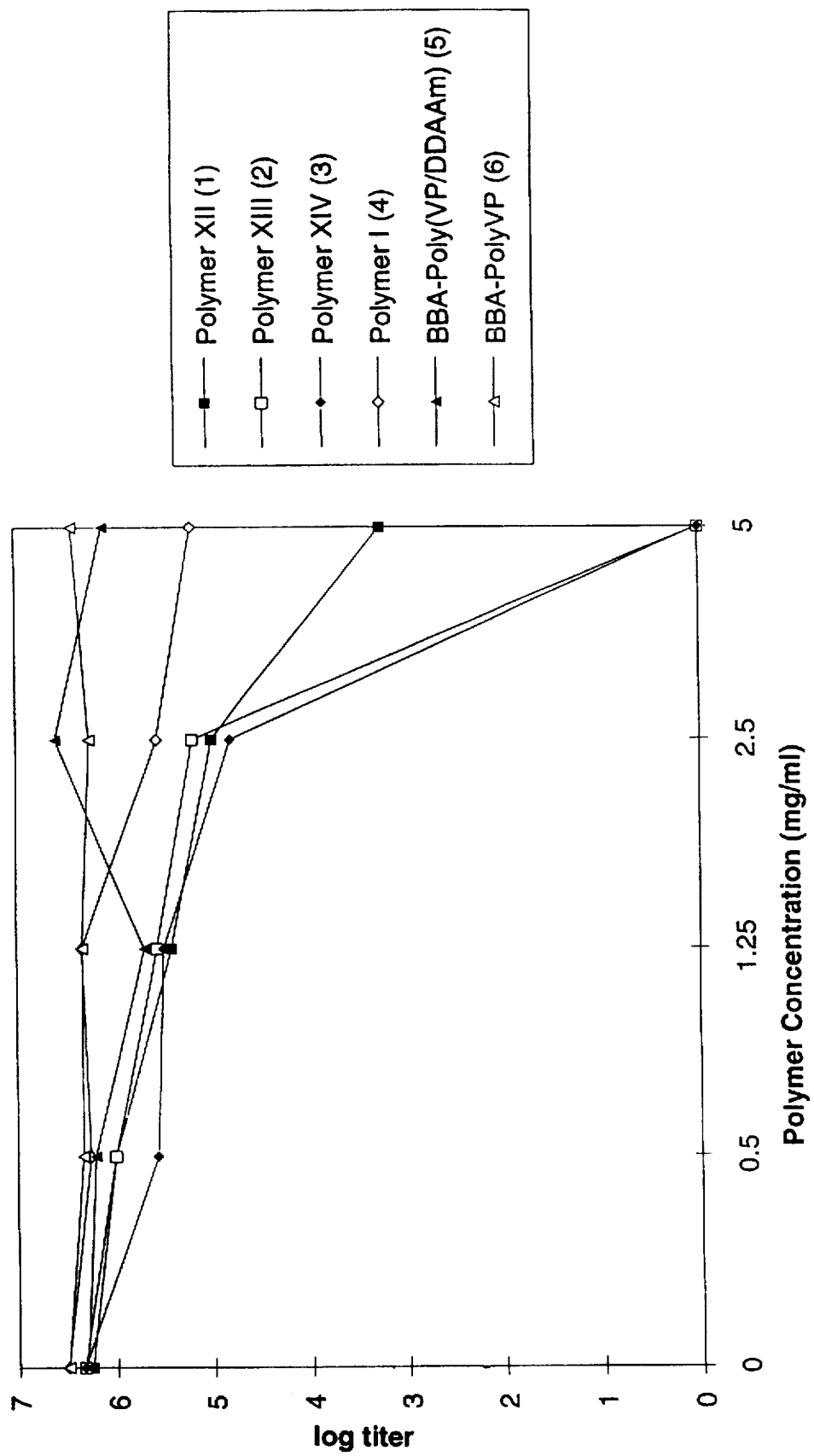
FIG. 1 represents a plot of polymer concentration versus log titer for the results described in Example 8.

The present invention provides a virus contacting article formed of a fabric substrate bearing an immobilized polymeric coating that exhibits antiviral activity against viruses. As used herein, the following words and phrases will have the meaning ascribed below:

"Virus contacting article" will refer to an article intended or expected to be exposed to or come into physical contact with a virus such as a surface borne, liquid borne or air borne virus particle. Typically such an article will be used, at least in part, for protective purposes, and will be expected to inactivate viruses retained within the article.

"Fabric substrate" will refer to a flexible porous material (e.g., woven or nonwoven fabric, filter, or membrane) capable of being fabricated into a virus contacting article and also capable of being coating with a polymeric coating composition of the present invention.

"Absorbent" will refer to a hydrophilic or otherwise wettable porous substrate exhibiting the capacity suitable to allow the substrate to absorb and retain an aqueous vehicle such as a liquid, vapor, bodily fluid, and the like.

"Immobilized coating" refers to antiviral polymers attached to a fabric substrate in a nonleachable form, i.e., a form sufficiently stable for the use of the substrate for its intended purpose.

"Antiviral activity" will refer to the ability of an immobilized coating on a fabric substrate to inactivate substantially all lipid-enveloped virus particles in an absorbed aqueous vehicle.

"Photopolymer" refers to a polymer having one or more attached latent reactant groups.

"Latent reactive group" as used herein, refers to a chemical group that responds to an applied external energy source in order to undergo active specie generation, resulting in covalent bonding to an adjacent chemical structure (e.g., a carbon with an abstractable hydrogen).

"Virus", and inflections thereof, refers to a virus having the ability to cause disease, while "nonpathogenic" will refer to a virus that has been rendered inactive by the method or article of the present invention.

Fabrics

Fabric substrates for use in preparing medical articles of the present invention can be provided in a variety of types and forms. Suitable substrates include porous materials capable of being fabricated into an article of choice, and of having photopolymer attached thereto. Such substrates are either inherently absorbent, or capable of being rendered absorbent by the attachment of suitable hydrophilic photopolymers.

Suitable substrates include fabrics formed from textiles (e.g., knitted, woven or bonded fabrics) as well as nonwoven fabrics formed of fibers assembled in webs. Other porous materials, such as filters and membranes, are also suitable for use in preparing medical articles of the invention.

Fabrics can be formed using conventional textiles, including cellulosics, cotton, synthetics, proteins, glasses, and blends. Woven fabrics can also be used and include such materials as cotton, polyester, nylon, acetate and wool.

Preferred fabrics include nonwoven fabrics, such as webs made by processes such as melt blown, spun bond, spun laced and needle punching (See, for example, Nonwovens Industry, March: 50 (1994)). Examples of preferred materials out of which nonwoven fabrics can be made include polypropylene (PP), polyester (PES), rayon, nylon, acrylic, polyvinyl chloride (PVC), and blends thereof.

Fabric substrates are modified by covalently attaching to the substrate photoactivatable hydrophilic polymers containing both cationic (e.g., quaternary ammonium) groups and hydrocarbon chains. In turn, viruses such as lipid-enveloped viruses that are absorbed into the material are inactivated by disruption of the lipid envelope. Preferred fabrics are therefore wettable, or capable of being rendered wettable by the immobilized polymers themselves, thereby allowing the fabric to absorb aqueous vehicles containing the virus to be inactivated.

Articles

The present invention can be used to prepare protective, e.g., medical, articles in a variety of shapes, styles, and sizes, and for protection against exposure to a variety of viruses.

Suitable medical articles include patient care articles such as wound and burn coverings, closures, and dressings, as well as surgical articles such as sterilizable instrument wraps, tapes, gowns, drapes, masks, wraps and sponges for use on or by a health care professional in the course of invasive surgery and similar procedures. Preferably the articles are sterilizable prior to use, and are often disposable after use. Other suitable articles include filters, membranes, and other similar products used for the preparation (e.g., purification) of products such as blood and its components.

Polymers/Polymeric Backbones

A preferred photopolymer of the present invention is provided in the form of a polymeric backbone bearing a plurality of viral inactivating groups and also bearing one or more latent reactive groups for attaching the polymer to a substrate. Typically, and preferably, both the inactivating groups and latent reactive groups are pendant to the backbone. Preferred photoactivatable hydrophilic polymers contain both cationic groups and hydrocarbon chains that together provide a localized surfactant activity capable of disrupting the lipid envelopes of viruses.

Formula 1 below depicts a general formula for preferred photopolymers wherein the cationic groups and hydrocarbon chains are each provided on different monomer units, while Formula 2 depicts a photopolymer wherein cationic groups and hydrocarbon chains are both provided on the same monomer units. Those skilled in the art, given the present description, will be able to identify and prepare polymers having cationic groups and hydrocarbon chains in sufficient numbers and proximity to allow them to provide a desired level of antiviral activity.

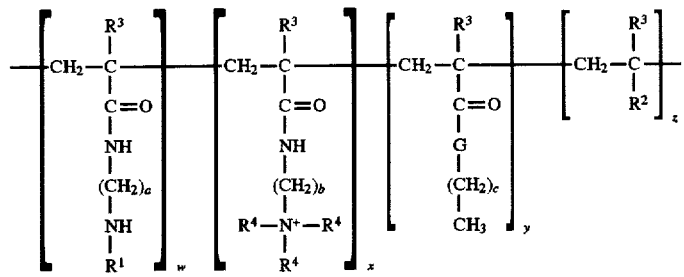

FORMULA 1

Referring first to Formula 1, this Formula portrays the structure of a photopolymer containing quaternary ammonium salt and hydrocarbon chain on different monomer units. In Formula 1, $R^1$ is a latent reactive group (e.g., aryl azide or aryl ketone),
$R^2$ is N-pyrrolidone or carboxamide,
each $R^3$ independently is H or methyl,
each $R^4$ independently is an alkyl group having 1 to 4 carbon atoms,
G is —NH— or —O—,
a is a whole number from 2 to 10,
b is a whole number from 2 to 10,
c is a whole number from 10 to 24 or a monounsaturated analog having from 10 to 24 carbon atoms, and
w is 0.5–5%, x is 1–10%, y is 1–10% and z is 75 to 97% per 100 monomer units, wherein the monomers can be randomly distributed along the polymer backbone.

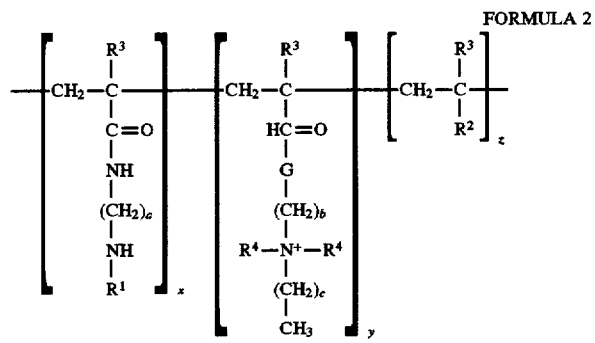

FORMULA 2

Referring to Formula 2 above, there is shown the structure of a preferred photopolymer containing both quaternary ammoniums and hydrocarbon chains on the same monomer units, wherein each of $R^1$ through $R^4$, G and (a) through (c) are as described above, and x is 0.5–5%, y is 1–10% and z is 85–98% per 100 monomer units, wherein the monomers can be randomly distributed along the polymer backbone.

Examples of suitable polymeric backbones include polyvinylpyrrolidone (PVP), polyacrylamide (PAAm), poly-N-acryloyl-tris(hydroxymethyl)aminomethane (PNAT), and the like.

In one embodiment, a suitable polymeric backbone is provided in the form of a copolymer of N-vinylpyrrolidone, N-(n-octadecyl)acrylamide (ODAAm), 3-(methacrylamido)propyltrimethylammonium chloride (MAAmPTAC) and N-[3-(4-benzoylbenzamido)propyl]methacrylamide (NBBAPMAAm) (See Formula 1). Such a polymer can be photoimmobilized, for instance, onto an otherwise hydrophobic fabric formed of melt blown polypropylene in order to provide both absorbency and antiviral activity.

In another embodiment of the invention, a suitable polymer is provided in the form of a copolymer of N-vinylpyrrolidone, 3-(methacrylamido)propylstearyldimethylammonium chloride (MAAmPSDAC) and NBBAPMAAm. This polymer can be photocoupled, for instance to melt blown polypropylene fabric, in order to render the fabric absorbent and have antiviral activity (Formula 2). The MAAmPSDAC is preferably between 1 and 10 mole percent of total monomer and the NBBAPMAAm is preferably between 0.5 and 5 mole percent of total monomer. Most preferably, the MAAmPSDAC is present in an amount between about 2% and about 3 %, by weight, and the NBBAPMAAm is present in an amount between about 1 % and about 2 % of total monomer.

In one embodiment of this invention, melt blown polypropylene was coated with photoactivatable, hydrophilic polymers having both cationic groups and hydrocarbon chains. These polymers rendered the fabric wettable and were also shown to inactivate vesicular stomatitis virus (VSV) in solution. When immobilized onto the fabric, the virus was absorbed into the fabric and inactivated.

Antiviral Activity

Antiviral activity of the present invention can be provided in any suitable manner, and is preferably provided by the use of one or more pendant groups capable of exhibiting antiviral activity when attached to the polymer backbone. Antiviral activity can be provided by the use of a single type of pendant group, such as a cationic detergent. Preferably antiviral activity is provided by the use of a two component system including both cationic groups (e.g., quaternary ammonium groups) and hydrocarbon chains. While not intending to be bound by theory, it appears that the hydrocarbon chains function to attract and/or embed themselves in the hydrophobic (e.g., lipid) viral envelope, whereupon nearby ionic groups then function by disrupting lipid in order to inactivate the virus.

Preferably the articles are used for exposure or contact with lipid-enveloped viruses, including enveloped complex viruses (poxyiruses), enveloped icosahedral (herpes viruses, togaviruses), and enveloped helical viruses (orthomyxoviruses, paramyxoviruses, coronaviruses, rhabdoviruses, arenaviruses, retroviruses). In a particularly preferred embodiment, the articles are used for exposure or contact with the HIV and hepatitis B viruses.

Suitable antiviral groups include quaternary ammonium groups and other cationic groups such as phosphonium compounds. Quaternary ammonium groups include alkyl ammonium compounds as well as aromatic quaternary ammonium groups such as pyridinium compounds. Alkyl ammonium compounds can include derivatives of choline, betaine, muscarine, benzalkonium, benzethonium, methylbenzenethonium, decamethoniun, hexamethonium, and the like. A review of quaternary ammonium antiviral compounds is provided in Chapter 13 of *Disinfection Sterilization and Preservation*, 4th Edition, S. S. Block, ed., Lea & Febiger (Philadelphia) 1991, pp. 225–255, the disclosure of which is incorporated herein by reference. Phosphonium compounds include [tributyl( 4-vinylbenzyl)phosphonium chloride], and are described in *J. Appl. Polymer Sci.* 53:1237 (1994), the disclosure of which is also incorporated by reference.

A variety of pendant hydrocarbon chains can be used in conjunction with the quaternary ammonium groups. Suitable hydrocarbon chains can include, for instance, portions of saturated fatty acid analogues or corresponding hydrocarbon chains, such as decane, dodecane, tetradecane, hexadecane, octadecane, eicosane, docosane and tetracosane.

The chains can also be provided by unsaturated hydrocarbons (e.g., alkenes) derived from fatty acids, such as palmitoleic, oleic, linoleic, linolenic and arachidonic. Branched hydrocarbons such as t-butyl and isoamyl groups can also be used. Other suitable nonpolar functionalities include aromatic groups, such as phenyl groups.

Latent Reactive Groups

Hydrophilic antiviral polymers of the present invention are preferably immobilized by photochemical coupling to the fabric surface. Photochemical coupling can be achieved with photoactivatable groups, including aryl ketones such as derivatives of benzophenone, and aryl azides such as azidonitrophenyl groups.

Preferred latent reactive groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Latent reactive groups respond to energy from external stimuli to undergo active specie generation with resultant covalent bonding to an adjacent chemical structure, e.g., as provided by the same or a different molecule. Latent reactive groups are those groups of atoms in a molecule that retain their covalent bonds unchanged under conditions of storage but that, upon activation by an external energy source, form covalent bonds with other molecules.

The latent reactive groups generate active species such as free radicals and particularly diradicals such as nitrenes, carbenes, and excited states of ketones upon absorption of external electric, electromagnetic or kinetic (thermal) energy. Latent reactive groups may be chosen to be responsive to various portions of the electromagnetic spectrum, and latent reactive groups that are responsive to e.g., ultraviolet and visible portions of the spectrum are preferred and are referred to herein occasionally as "photochemical" groups.

Photoreactive aryl ketones such as acetophenone and benzophenone, or their derivatives, are preferred, since these functional groups, typically, are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light induced excitation of the benzophenone group is reversible and the molecule returns to ground state energy level. Hence, photoreactive aryl ketones are particularly preferred.

The azides constitute a preferred class of latent reactive groups and include aryl azides

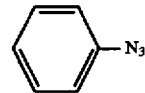

such as phenyl azide and particularly 4-fluoro-3-nitrophenyl azide, acyl azides

such as benzoyl azide and p-methylbenzoyl azide, azidoformates

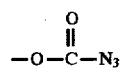

such as ethyl azidoformate and phenyl azidoformate, sulfonyl azides

such as benzenesulfonyl azide, and phosphoryl azides

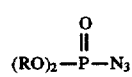

such as diphenyl phosphoryl azide and diethyl phosphoryl azide. Diazo compounds constitute another class of latent reactive groups and include diazoalkanes (—CHN₂) such as diazomethane and diphenyldiazomethane, diazoketones

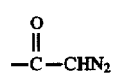

such as diazoacetophenone and 1-trifluoromethyl-1-diazo-2-pentanone, diazoacetates

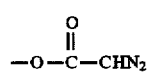

such as t-butyl diazoacetoacetate and phenyl diazoacetate, and beta-keto-alpha-diazoacetates

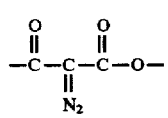

such as t-butyl alpha diazoacetoacetate. Other latent reactive groups include the aliphatic azo compounds such as azobis-cyanovaleric acid, the diazirines

such as 3-trifluoromethyl-3-phenyldiazirine, and the ketenes (—CH=C=O) such as ketene and diphenylketene. Photoactivatable aryl ketones such as benzophenone and acetophenone are of particular importance inasmuch as these groups are subject to multiple reactivation in water and hence provide increased coating efficiency. Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

Upon activation of the latent reactive groups, the coating compounds are covalently bound to each other and/or to the surface of the article by covalent bonds through residues of the latent reactive groups. Exemplary latent reactive groups, and their residues upon activation, are as follows:

TABLE 1

List of Abbreviations

| Abbreviation | Full Name |
|---|---|
| AAm | Acrylamide |
| AIBN | 2,2'-Azobisisobutyronitrile |
| BBA | Benzoylbenzoic acid |
| DA | n-Decyl acrylate |
| DAAm | N-(n-Decyl)acrylamide |
| DD | Dodecyl |
| DDA | Dodecylamine |
| DDAAm | N-(n-Dodecyl)acrylamide |
| DMF | N,N-Dimethylformamide |
| MAAmPDDDAC | 3-(Methylacrylamido)propyl-n-dodecyldimethylammonium chloride |
| MAAmPPDDAC | 3-(Methacrylamido)propyl-n-pentadecyldimethylammonium chloride |
| MAAmPSDAC | 3-(Methacrloylamido)propylstearyldimethylammonium chloride |
| MAAmPTAC | 3-(Methacrylamido)propyltrimethylammonium chloride |
| MEM | Minimal Essential Medium |

| Latent Reactive Group | Residue | Functionality |
|---|---|---|
| aryl azides | amine | R—NH—R' |
| acyl azides | amide | R—C(=O)—NH—R' |
| azidoformates | carbamate | R—O—C(=O)—NH—R' |
| sulfonyl aides | sulfonamide | R—S(=O)(=O)—NH—R' |
| phosphoryl azides | phosphoramide | (RO)$_2$—P(=O)—NH—R' |
| diazoalkanes | new C—C bond | |
| diazoketones | new C—C bond & ketone | |
| diazoacetates | new C—C bond & ester | |
| beta-keto-alpha-diazoacetates | new C—C bond & beta-ketoester | |
| aliphatic azo | new C—C bond | |
| diazirines | new C—C bond | |
| ketenes | new C—C bond | |
| photoactivated ketones | new C—C bond & alcohol | |
| dialkyl peroxides | ethers | |
| diacyl peroxides | esters & new C—C bonds | |
| peroxyesters | ethers, esters, and new C—C bonds | |

EXAMPLES

The following Examples are provided to illustrate, but not limit, the scope of the invention. Unless otherwise specified, all parts and percentages are by weight. For use in the Examples, Table 1 is provided below with a list of abbreviations of terms and Table 2 is provided with a list of polymers.

TABLE 1-continued

List of Abbreviations

| Abbreviation | Full Name |
|---|---|
| NBBAPMAAm | N-[3-(4-benzobenzamido)propyl]methacrylamide |
| NNNDAPMAAm | N-[3-(N,N-Dimethylamino)propyl]methacrylamide |
| OA | N-(n-oleyl)amine |
| OAAm | N-(n-oleyl)acrylamide |
| ODAAm | N-(n-octadecyl)acrylamide |
| PAAm | Polyacrylamide |
| PD | Pentadecyl |
| PEO | Poly(ethylene oxide) |
| PES | Polyester |
| PNAT | Poly-N-acryloyl-tris(hydroxymethyl)aminomethane |

TABLE 1-continued

List of Abbreviations

| Abbreviation | Full Name |
|---|---|
| PP | Polypropylene |
| PVC | Polyvinyl chloride |
| PVP | Polyvinylpyrrolidone |
| Quat | Quaternary ammonium salts |
| SA | Stearyl acrylate |
| TEMED | N,N,N',N'-Tetramethylethylenediamine |
| VP | N-vinylpyrrolidone |
| VSV | Vesicular Stomatitis Virus |

TABLE 2

List of Polymers

| Polymer | Polymer Name |
|---|---|
| I | BBA-Poly(VP/MAAmPTAC(Quat)/DDAAm) (1% BBA, 2% Quat, 2% DDAAm) |
| II | BBA-Poly(VP/MAAmPTAC(Quat)/DDAAm) (1% BBA, 2% Quat, 3% DDAAm) |
| III | BBA-Poly(VP/MAAmPTAC(Quat)/ODAAm) (1% BBA, 2% Quat, 1% ODAAm) |
| IV | BBA-Poly(VP/MAAmPTAC(Quat)/DAAm) (1% BBA, 2% Quat, 2% DAAm) |
| V | BBA-Poly(VP/MAAmPTAC(Quat)/SA) (1% BBA, 2% Quat, 2% SA) |
| VI | BBA-Poly(VP/MAAmPTAC(Quat)/SA) (1% BBA, 4% Quat, 2% SA) |
| VII | BBA-Poly(VP/MAAmPTAC(Quat)/DA) (1% BBA, 2% Quat, 2% DA) |
| VIII | BBA-Poly(AAm/MAAmPTAC(Quat)/OAAm) (1% BBA, 4% Quat, 2% OAAm) |
| IX | BBA-Poly(AAm/MAAmPTAC(Quat)/OAAm) (1% BBA, 2% Quat, 2% OAAm) |
| X | BBA-Poly(AAm/MAAmPSDAC) (1% BBA, 2% MAAmPSDAC) |
| XI | BBA-Poly(AAm/MAAmPSDAC) (1% BBA, 3% MAAmPSDAC) |
| XII | BBA-Poly(VP/MAAmPDDDAC) (1% BBA, 2% MAAmPDDDAC) |
| XIII | BBA-Poly(VP/MAAmPPDDAC) (1% BBA, 2% MAAmPPDDAC) |
| XIV | BBA-Poly(VP/MAAmPSDAC) (1% BBA, 2% MAAmPSDAC) |

The invention will be further illustrated by the following nonlimiting examples. Example 1 describes the synthesis of a photoactivatable, virucidal polyvinyl pyrrolidone based polymer having cationic groups and saturated hydrocarbon chains on separate monomer units. Example 2 describes the synthesis of several other virucidal, photoactivatable polyvinyl pyrrolidone based polymers having cationic groups and saturated hydrocarbon chains on separate monomer units. Example 3 describes the synthesis of a photoactivatable, virucidal polyacrylamide based polymer having cationic groups and unsaturated hydrocarbon chains on separate monomer units. Example 4 describes another photoactivatable, virucidal polyacrylamide based polymer having cationic groups and unsaturated hydrocarbon chains on separate monomer units. Example 5 describes the synthesis of a photoactivatable, virucidal polyacrylamide having cationic groups and hydrocarbon chains on the same monomer units. Example 6 describes the synthesis of another photoactivatable, virucidal polyacrylamide having cationic groups and hydrocarbon chains on the same monomer units. Example 7 describes the synthesis of photoactivatable, virucidal polyvinylpyrrolidone having cationic groups and hydrocarbon chains on the same monomer units. Example 8 describes the method for testing photopolymers for virucidal activity and some data generated from one experiment with several polymers. It can be seen that various photopolymers having both cationic groups and hydrocarbon chains exhibit virucidal activity in solution. Example 9 describes an experiment to demonstrate virucidal activity with a virucidal polymer immobilized on a fabric. It can be seen that the fabric coated with a virucidal polymer reduced the activity of virus that was exposed to the fabric.

Example 1

Synthesis of BBA-Poly(VP/MAAmPTAC(Quat)/DDAAm) (Polymer I)

Into 2 ml of DMF, previously stored over molecular sieves and a cation exchanger, was dissolved 37 mg (0.20 mmole) of DDA. To this solution was added 18 mg (0.20 mmole) of acryloyl chloride and 33 mg (0.2 mmole) of triethylamine that had been stored over molecular sieves. The solution was stirred for 1 hour at room temperature. In another vial, 1 gm (9.3 mmole) of N-vinylpyrrolidone was dissolved in 10 ml of DMF. To this solution was added 44 mg (0.2 mmole) of MAAmPTAC (Quat). The two solutions were combined and 35 mg (0.1 mmole) of NBBAPMAAm was added. In addition, 100 mg of AIBN and 45 μl of TEMED were added. After bubbling nitrogen gas through the solution, it was tightly capped and put at 55° C. overnight. The resulting polymer solution was dialyzed against deionized water, then lyophilized.

Example 2

Synthesis of Other Poly VP Polymers Containing Quaternary Ammonium Salts and Hydrocarbon Chains on Separate Monomer Units (Polymers II-VII)

The method described in Example I was repeated for Polymers II-VII except that the concentration of the Quat was varied in Polymer II and different hydrocarbon chain monomers were used in preparing Polymers II-VII. Also the ester analogues of Polymers V-VII were prepared using the commercially available SA and DA monomers (Scientific Polymer Products, Inc., Ontario, N. Y.), thus eliminating the need to react fatty acid amine with acryloyl chloride.

Example 3

Synthesis of BBA-poly(AAm/MAAmPTAC(Quat)/OAAm) (Polymer VIII)

Into 2 ml of DMF stored over molecular sieves and a cation exchanger was dissolved 123 μl of oleylamine (OA) (0.30 mmole). To this solution was added 25 μl of acryloyl chloride (0.307 mmole) and 60 μl of triethylamine (0.325 mmole) that had been stored over molecular sieves. The solution was stirred for one hour followed by addition of 132 mg (0.60 mmole) MAAmPTAC (Quat). The OAAm+Quat solution was diluted into 15 ml of tetrahydrofuran (THF). To this solution was added 1.0 gm (14.1 mmole) of acrylamide, 50 mg (0.14 mmole) of NBBAPMAAm, 100 mg of AIBN and 50 μl of TEMED. The solution was then bubble with $N_2$ and heated at 55° C. overnight to polymerize. The polymer solution was then dialyzed against deionized water, then lyophilized.

Example 4

Synthesis of Poly Aam Polymers Containing Quaternary Ammonium Salts and Hydrocarbon Chains on Separate Monomer Units (Polymer IX)

The method of Example 3 was repeated for Polymer IX except that the concentration of Quat and OA was changed.

Example 5
Synthesis of BBA-Poly(AAm/MAAmPSDAC) (Polymer X)

Monomers having both quaternary amine and alkane on the same monomer unit were prepared by reacting the alkyl bromides of alkanes, such as stearyl bromide, with NNNDAPMAAm in anhydrous THF overnight at room temperature. The products were confirmed by nuclear magnetic resonance spectrometry (NMR).

One gram (14.1 mmoles) of acrylamide was dissolved in 15 ml THF. To this solution was added 151 mg (0.30 mmole) of MAAmPSDAC, 53 mg (0.15 mmole) of NBBAPMAA, 100 mg AJBN and 50 μl of TEMED. After bubbling nitrogen through the solution, it was tightly capped and allowed to polymerize overnight at 55° C. The polymer, which precipitated upon reaching a certain molecular weight, was collected by filtration, dissolved in deionized water, dialyzed against deionized water and lyophilized.

Example 6
Synthesis of PolyAAm Polymers Containing Quaternary Ammonium Salt and Hydrocarbon Chain on the Same Monomer Unit (Polymer XI)

The method of Example 5 was repeated for Polymer XI except that the concentration of MAAmPSDAC was increased from 2 to 3%.

Example 7
Synthesis of Poly VP Polymers Containing Quaternary Ammonium Salts and Hydrocarbon Chains on the Same Monomer Units (Polymers XII–XIV)

The method of Example 5 was repeated for Polymers XII–XIV except the VP polymerizations were carried out in DMF and the hydrocarbon chain on the combined Quat plus hydrocarbon chain was either dodecyl, pentadecyl, or stearyl.

Example 8
Testing Photopolymers for Virucidal Activity

The hydrophilic polymers were primarily tested for virucidal activity in solution using vesicular stomatitis virus (VSV—Indiana Strain) as a model lipid-coated virus. VSV was obtained from the American Type Culture Collection (ATCC #VR-158), aliquoted, and kept frozen at −70° C. until just prior to use. Virus was incubated with the polymers for a specific time. NCTC 929 (L929) cells were suspended in media at $1.0 \times 10^4$ cells/ml and plated in wells of 96-well plates in 200 μl aliquots. Cultures were incubated for 3 hours at 37° C. in a 5% $CO_2$ environment in Minimal Essential Medium (MEM) supplemented with 10% equine serum, plus 100 μg/ml streptomycin, 100 units/ml penicillin and 250 ng/ml amphotericin B. Virus biological activity was determined by inoculating eight replicate wells of the NCTC 929 cultures with serial dilutions of the virus or virus/polymer mixtures. After inoculation, the cells were cultured for 72 hours at 37° C. in 5 % $CO_2$, then scored for virus induced cytopathology.

To determine the time required for inactivation, virus was incubated with polymers for varying times at a single concentration. The polymer series of the type shown in Formula 2 (Polymers XII–XIV) were incubated at 10 mg/ml with virus for varying times ranging down to 5 minutes. Each of the polymers inactivated the virus with each exposure time. In a follow-up experiment, Polymer XIII was incubated for varying times down to 10 seconds. At 10 mg/ml, this polymer inactivated the virus in 10 seconds, the shortest time tested.

Virucidal assay was performed using a variety of photopolymers of the present invention. The results are presented in FIG. 1, wherein: plots (1)–(3) represent photo PVP having alkane and quaternary ammonium groups on the same monomer unit, plot (4) represents photo PVP having alkane and quaternary ammonium groups on separate monomer units, plot (5) represents photo PVP having only alkane groups (i.e., no quaternary ammonium groups), and plot (6) represents a photo PVP control (no alkane or quaternary ammonium groups). It can be seen that polymers having both quaternary ammonium groups and alkanes attached to the same monomer units are most effective in inactivating virus.

Example 9
Demonstration of Virucidal Activity with Melt Blown Polypropylene Fabric having Immobilized Virucidal Polymer Melt blown polypropylene having a weight basis of 3 oz/sq yd was first plasma treated (oxygen plasma for 1.5 min. at 250 watts) in order to render it temporarily wettable to the coating reagents. Solutions of the hydrophilic polymers were prepared in deionized water and applied to the plasma treated fabric by soaking for a few minutes. After photopolymer application, excess solution was drained, and the fabric was illuminated with ultraviolet light for two minutes. Any nonimmobilized polymer was washed from the fabric after which it was dried for testing or for further coating. Varying concentrations, application times, and conditions (e.g., solvent) were evaluated to optimize the coating. The fabric could also be coated without plasma pretreatment by prewetting the fabric with alcohol solution or even by squeezing the fabric in the polymer solution.

NCTC 929 (L929) cells were plated in wells of a 96-well plate at a concentration of $1 \times 10^4$ cells/ml in 200 μA of media. Cultures were incubated for 3 hours at 37° C. in a 5% $CO_2$ environment in MEM supplemented with 10% fetal bovine serum, plus 100 μg/ml streptomycin, 100 units/ml penicillin and 250 ng/ml amphotericin B. VSV was thawed at 37° C. and diluted to $10^{-3}$ of the original stock concentration. The virus suspension (250 l) was pipetted in 10 μl increments onto 3 cm×3 cm pieces of fabric coated at 10 mg/ml with either photo-PVP or Polymer XIV. The pieces were covered in sterile 6-well tissue culture plates to prevent drying and allowed to incubate for 1 hour. Each sample was then washed with 2.25 ml of media and vortexed for 30 seconds in a sterile 50 ml centrifuge tube. Media was then squeezed out of the fabric samples, diluted serially and 200 μl was plated on eight replicate wells containing the established NCTC cells. After inoculation, the cells were cultured for 72 hours at 37° C. in 5% $CO_2$. The cells were scored for virus induced cytopathology and the Tissue Culture Infective Dose ($TCID_{50}$) was calculated. The viral titer of the incubated samples was plotted versus the untreated virus titer. The viral titer from Polymer XIV was significantly lower than that of the control fabric having photo PVP immobilized at the same concentration.

While a preferred embodiment of the present invention has been described, it should be understood that the various changes, adaptations and modifications may be made therein without departing from the spirit of the invention and the scope of the appended claims.

What is claimed is:

1. An article useful for inactivating viruses upon contact, the article comprising a fabric substrate bearing a coating of immobilized polymer molecules that provides the substrate with nonleachable antiviral activity, wherein the polymer molecules comprise a hydrophilic polymer having pendant antiviral groups comprising a plurality of pendant cationic groups and a plurality of pendant hydrocarbon chains, and wherein the pendant cationic groups are, independently, selected from the group consisting of quaternary ammonium groups and phosphonium groups.

2. An article according to claim 1 wherein the polymer molecules are immobilized to the substrate by the residues of activated pendant photochemically reactive groups.

3. An article according to claim 1 wherein the residues are of photochemically reactive groups selected from the group consisting of aryl ketones and aryl azides.

4. An article according to claim 3 wherein the residues comprise residues of benzophenone.

5. An article according to claim 1 wherein the fabric substrate comprises a porous fabric or porous membrane.

6. An article according to claim 5 wherein the fabric substrate is a nonwoven polyolefin.

7. An article according to claim 6 wherein the nonwoven polyolefin is a melt blown polypropylene.

8. An article according to claim 1 wherein the hydrophilic polymer comprises a copolymer of vinylpyrrolidone or acrylamide.

9. An article according to claim 1 wherein the pendant hydrocarbon chains are selected from the group consisting of $C_{10}$ to $C_{24}$ saturated alkanes and $C_{10}$ to $C_{24}$ monounsaturated alkenes.

10. An article according to claim 1 wherein the quaternary ammonium groups and hydrocarbon chains are both pendant on the same monomer units of the polymer backbone.

11. An article according to claim 1 wherein the quaternary ammonium groups and hydrocarbon chains are pendant on different monomer units of the polymer backbone.

12. An article according to claim 1 wherein the antiviral coating is effective against lipid enveloped viruses.

13. An article according to claim 12 wherein the lipid enveloped viruses are HIV or hepatitis viruses.

14. An article according to claim 1 wherein the article is selected from the group consisting of surgical gowns, surgical drapes, surgical masks and wound dressings.

15. An article according to claim 1 wherein the polymer comprises four monomers and the bound residues of pendant photochemically reactive groups, the polymer being of the formula:

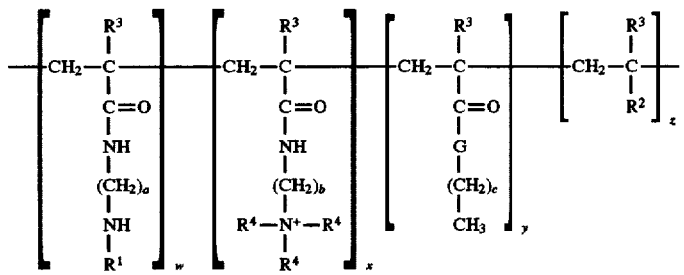

wherein:

$R^1$ is a latent reactive group, $R^2$ is N-pyrrolidone or carboxamide, each $R^3$ independently is H or methyl, each $R^4$ independently is an alkyl group having 1 to 4 carbon atoms, G is —NH— or —O—, a is a whole number from 2 to 10, b is a whole number from 2 to 10, c is a whole number from 10 to 24 or a monounsaturated analog having from 10 to 24 carbon atoms, and w is 0.5–5%, x is 1–10%, y is 1–10% and z is 75 to 97% per 100 monomer units, wherein the monomers can be randomly distributed along the polymer backbone.

16. An article according to claim 1 wherein the polymer comprises three monomers and the bound residues of pendant photochemically reactive groups, the polymer being of the formula:

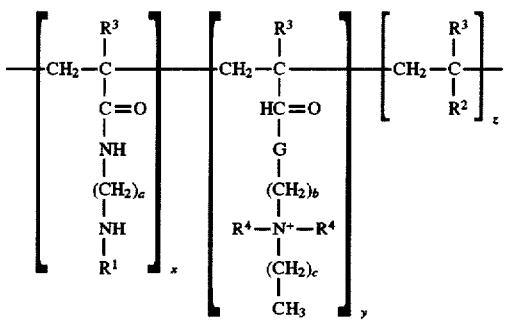

wherein:

$R^1$ is a latent reactive group, $R^2$ is N-pyrrolidone or carboxamide, each $R^3$ independently is H or methyl, each $R^4$ independently is an alkyl group having 1 to 4 carbon atoms, G is —NH— or —O—, a is a whole number from 2 to 10, b is a whole number from 2 to 10, c is a whole number from 10 to 24 or a monounsaturated analog having from 10 to 24 carbon atoms, and x is 0.5–5%, y is 1–10% and z is 85–98% per 100 monomer units, wherein the monomers can be randomly distributed along the polymer backbone.

17. An article useful for inactivating viruses upon contact, the article comprising a fabric substrate bearing a coating of immobilized polymer molecules that provides the substrate with nonleachable antiviral activity, wherein the polymer molecules comprise a hydrophilic polymer having pendant antiviral groups comprising a plurality of pendant cationic groups and a plurality of pendant hydrocarbon chains, and wherein the polymer molecules further comprise the residues of pendant photochemically reactive groups, selected from the group consisting of aryl ketones and aryl azides, that have being activated in order to covalently immobilize the polymer molecules to the substrate.

18. An article according to claim 17 wherein the pendant cationic groups are, independently, selected from the group consisting of quaternary ammonium groups and phosphonium groups.

19. An article according to claim 18 wherein the pendant cationic groups are quaternary ammonium groups.

20. An article according to claim 17 wherein the residues comprise residues of photochemically reactive aryl ketones.

21. An article according to claim 20 wherein the residues comprise residues of benzophenone.

22. An article according to claim 17 wherein the fabric substrate comprises a porous fabric or porous membrane.

23. An article according to claim 22 wherein the fabric substrate is a nonwoven polyolefin.

24. An article according to claim 23 wherein the nonwoven polyolefin is a melt blown polypropylene.

25. An article according to claim 17 wherein the hydrophilic polymer comprises a copolymer of vinylpyrrolidone or acrylamide.

26. An article according to claim 17 wherein the pendant hydrocarbon chains are selected from the group consisting of $C_{10}$ to $C_{24}$ saturated alkanes and $C_{10}$ to $C_{24}$ monounsaturated alkenes.

27. An article according to claim 19 wherein the quaternary ammonium groups and hydrocarbon chains are both pendant on the same monomer units of the polymer backbone.

28. An article according to claim 19 wherein the quaternary ammonium groups and hydrocarbon chains are pendant on different monomer units of the polymer backbone.

29. An article according to claim 17 wherein the antiviral coating is effective against lipid enveloped viruses.

30. An article according to claim 29 wherein the lipid enveloped viruses are HIV or hepatitis viruses.

31. An article according to claim 17 wherein the article is selected from the group consisting of surgical gowns, surgical drapes, surgical masks and wound dressings.

32. An article according to claim 17 wherein the polymer comprises four monomers and the bound residues of pendant photochemically reactive groups, the polymer being of the formula:

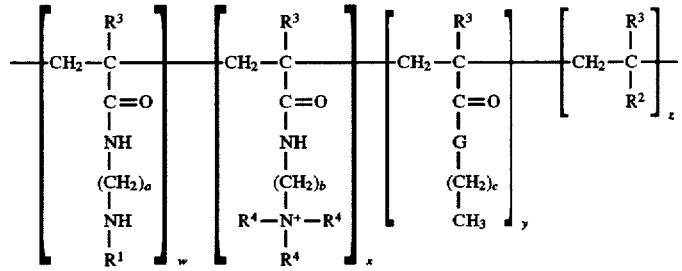

wherein:

$R^1$ is a latent reactive group, $R^2$ is N-pyrrolidone or carboxamide, each $R^3$ independently is H or methyl, each $R^4$ independently is an alkyl group having 1 to 4 carbon atoms, G is —NH— or —O—, a is a whole number from 2 to 10, b is a whole number from 2 to 10, c is a whole number from 10 to 24 or a monounsaturated analog having from 10 to 24 carbon atoms, and w is 0.5–5%, x is 1–10%, y is 1–10% and z is 75 to 97% per 100 monomer units, wherein the monomers can be randomly distributed along the polymer backbone.

33. An article according to claim 17 wherein the polymer comprises three monomers and the bound residues of pendant photochemically reactive groups, the polymer being of the formula:

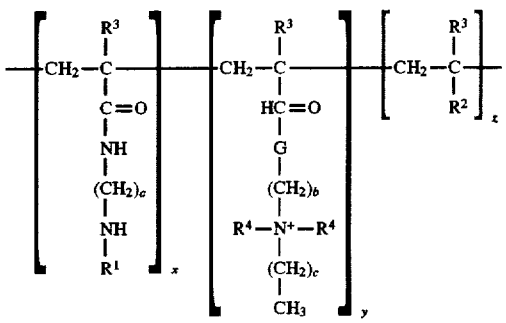

wherein:

$R^1$ is a latent reactive group, $R^2$ is N-pyrrolidone or carboxamide, each $R^3$ independently is H or methyl, each $R^4$ independently is an alkyl group having 1 to 4 carbon atoms, G is —NH— or —O—, a is a whole number from 2 to 10, b is a whole number from 2 to 10, c is a whole number from 10 to 24 or a monounsaturated analog having from 10 to 24 carbon atoms, and x is 0.5–5%, y is 1–10% and z is 85–98% per 100 monomer units, wherein the monomers can be randomly distributed along the polymer backbone.

* * * * *